(12) United States Patent
Graham

(10) Patent No.: US 8,931,808 B2
(45) Date of Patent: Jan. 13, 2015

(54) HIGH PRESSURE FITTING WITH SELF-RELEASING FERRULE

(75) Inventor: Craig W. Graham, Anacortes, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 508 days.

(21) Appl. No.: 13/038,110

(22) Filed: Mar. 1, 2011

(65) Prior Publication Data

US 2012/0223522 A1    Sep. 6, 2012

(51) Int. Cl.
*F16L 25/00* (2006.01)
*G01N 30/60* (2006.01)

(52) U.S. Cl.
CPC ................................. *G01N 30/6026* (2013.01)
USPC ............................ 285/332; 285/328; 285/330

(58) Field of Classification Search
USPC ........... 285/328, 330, 332, 332.1; 411/71, 78, 411/80.5, 383, 386
See application file for complete search history.

(56) References Cited

U.S. PATENT DOCUMENTS

| | | | | |
|---|---|---|---|---|
| 2,008,096 | A | * | 7/1935 | Clo ................................. 285/330 |
| 3,413,021 | A | * | 11/1968 | Potts .............................. 285/319 |
| 3,784,235 | A | | 1/1974 | Kessler et al. ................... 285/94 |
| 4,275,907 | A | * | 6/1981 | Hunt ................................. 285/18 |
| 4,669,761 | A | * | 6/1987 | Huling ........................... 285/330 |
| 5,525,303 | A | | 6/1996 | Ford et al. |
| 5,730,943 | A | | 3/1998 | Ford et al. |
| 6,095,572 | A | | 8/2000 | Ford et al. |
| 6,481,761 | B2 | * | 11/2002 | Schroeder et al. .......... 285/334.3 |
| 7,249,789 | B2 | * | 7/2007 | Haney et al. .................. 285/374 |
| 7,311,502 | B2 | | 12/2007 | Gerhardt et al. |
| 7,954,857 | B2 | | 6/2011 | Helstern |
| 7,984,933 | B2 | | 7/2011 | Helstern |
| 8,006,367 | B1 | | 8/2011 | Best |
| 2005/0269264 | A1 | | 12/2005 | Fermier et al. |
| 2007/0283746 | A1 | | 12/2007 | Gerhardt et al. |
| 2009/0295156 | A1 | | 12/2009 | Ford et al. |
| 2010/0102225 | A1 | | 9/2010 | Sanders |
| 2013/0298647 | A1 | | 11/2013 | Falk-Jordan |

FOREIGN PATENT DOCUMENTS

| | | |
|---|---|---|
| GB | 2482175 A | 1/2012 |
| WO | WO 2012/010222 A1 | 1/2012 |

OTHER PUBLICATIONS

International Search Report, International Patent Application No. PCT/US2012/027326, issued Jun. 11, 2012.
Co-Pending U.S. Appl. No. 13/292,667, filed Nov. 9, 2011.
International Search Report and Written Opinion of the International Searching Authority, International Patent Application No. PCT/US2012/027326, issued Jun. 11, 2012.

(Continued)

*Primary Examiner* — Aaron Dunwoody
*Assistant Examiner* — Fannie Kee
(74) *Attorney, Agent, or Firm* — Vinson & Elkins LLP

(57) ABSTRACT

A fitting assembly is provided having a nut and a self-releasing ferrule, which in certain embodiments may be assembled by an operator. The fitting assembly includes a nut with a first end, and a second end that defines a slot, and a ferrule with a first end that defines one or more slots, and a second end, with the second end of the nut adapted to receive the first end of the ferrule, the second end of the ferrule adapted to be received in a component or fitting of a liquid chromatography system. The nut and ferrule of the fitting assembly have passageways therethrough for receiving and removably holding tubing.

14 Claims, 9 Drawing Sheets

(56) References Cited

OTHER PUBLICATIONS

Sonntek, Inc., "Dynaseal A New HPLC Fitting Concept (Pat. Pending)", 1986.
Knauer, "Dynaseal", Chromatographia 21:713, 1986.
Sonnenschein and Knauer, "Dynaseal-Connection System for HPLC", Chromatographia 22:433, 1986.
Mellor, et al., "Supercritical fluid extraction using a new restrictor design", Journal of Chromatography A 679:147-152, 1994.
Knauer, "Product Catalog: HPLC Accessories", 50-58, 2003.
Optimize Technologies, "Product Catalog", 3-90, 2005.
"Products", LCGC North America 23, 312-330 (even numbered pages only), 2005.
Knauer, "HPLC System Spares & Accessories: 2007 Price List", Feb. 2007.
Knauer, "45 Years Knauer: 45 Years of Passion for Innovation" Knauer Company Overview Brochure, Jan. 2008.

* cited by examiner

HIGH PRESSURE FITTING WITH SELF-RELEASING FERRULE

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to an assembly for use in connecting components of liquid chromatography and other analytical systems, and relates more particularly to an assembly well-suited for allowing quick connections and disconnections of components in liquid chromatography systems used in high pressure and ultra-high pressure liquid chromatography.

2. Description of the Related Art

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" connections through the use of a material which is chemically inert with respect to such "biological" samples and the mobile phase used with such samples so that ions will not be released by the tubing and thus contaminate the sample.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate relatively high pressures of up to around 5,000 psi to 6,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Patent Publication No. US 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. US 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. US 2007/0283746 A1 and US 2005/0269264 A1.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an UHPLC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing. While hand-tightened threaded fittings eliminate the need for wrenches or other tools, these fittings typically can not stand up to the extreme pressures of HPLC or UHPLC.

Another approach to provide a connection in an UHPLC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effort to assemble them to make a connection or disassemble them when disconnecting tubing from a component or other fitting assembly.

It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said also has application to other types of AI systems and methods.

Therefore, it is an object of the present invention to provide a high pressure fitting with a self-releasing ferrule for use in a HPLC or an UHPLC system.

It is another object of the present invention to provide a high pressure fitting with a self-releasing ferrule that can hold to about 10,000 pounds per square inch ("psi") or more, and be reusable about 10 times or more.

It is another object of the present invention to provide a mechanism allowing an operator to quickly disconnect or connect a component of a HPLC or an UHPLC system.

It is another object of the present invention to provide a mechanism to reduce inefficiency and wasted time in connecting or disconnecting a component of a HPLC or an UHPLC system.

It is yet another object of the present invention to provide a mechanism to allow an operator to quickly replace a component of a HPLC or an UHPLC system.

It is yet another object of the present invention to provide a mechanism to allow an operator to quickly and easily achieve a leak-free connection of a component of a HPLC or an UHPLC system.

It is still another object of the present invention to provide a mechanism to minimize the risk of leakage or damage to the tubing of a HPLC or an UHPLC system.

It is still another object of the present invention to provide a biocompatible assembly to allow an operator to quickly and easily achieve a biocompatible connection of a component of a HPLC or an UHPLC system.

The above and other advantages of the present invention will become readily apparent to those skilled in the art from the following detailed description of the present invention, and from the attached drawings, which are briefly described below.

SUMMARY OF THE INVENTION

The present disclosure overcomes one or more of the deficiencies of the prior art by providing fitting assemblies with a self-releasing ferrule that are well-suited for use in liquid chromatography systems, and are particularly well-suited for use in high pressure and ultra high pressure liquid chromatography systems, such as HPLC and UHPLC.

The present disclosure provides a fitting assembly for use in a liquid chromatography system, comprising a nut having a first end and a second end, an externally threaded portion proximal the second end of the nut, having a passageway therethrough, wherein the passageway has an internally tapered portion, the nut having an internal lip proximal the second end of the nut, and wherein the nut defines a slot that extends from the second end of the nut through at least a portion of the externally threaded portion of the nut, and a ferrule having a first end, a first externally tapered portion, a central portion, a second externally tapered portion, and a second end, and having a passageway therethrough, wherein the first externally tapered portion of the ferrule is adapted to securely engage with the internally tapered portion of the passageway in the nut, wherein the first externally tapered portion and the central portion define a ferrule lip that securely engages the internal lip of the nut, wherein the ferrule defines at least a first slot that extends from the first end of the ferrule to at least the ferrule lip.

The present disclosure additionally provides a fitting assembly for use in a liquid chromatography system, comprising a nut having a first end, a second end, an externally threaded portion proximal to the second end, and having a passageway therethrough, wherein the passageway has an internally tapered portion having a wide end and a narrow end, and a lip proximal the narrow end of the internally tapered portion of the passageway in the nut, and wherein the nut defines a slot that extends from the second end of the nut through at least a portion of the externally threaded portion, and a ferrule having a first end, a first non-tapered portion, a second non-tapered portion, a first externally tapered portion, a third non-tapered portion, a second externally tapered portion, and a second end, and having a passageway therethrough, wherein the first externally tapered portion of the ferrule is adapted to securely engage with the internally tapered portion of the passageway in the nut, wherein the first non-tapered portion and the second non-tapered portion define a ferrule lip that securely engages the lip of the nut, and wherein the ferrule defines at least a first slot that extends from the first end of the ferrule to at least the third non-tapered portion of the ferrule.

In certain embodiments the ferrule defines a plurality of slots that extend from the first end of the ferrule to at least the ferrule lip or beyond. In particular embodiments the ferrule defines one slot, two slots, four slots, or six slots that extend from the first end of the ferrule to at least the ferrule lip or beyond. In other embodiments of the fitting assemblies of the present disclosure, the nut and the ferrule may rotate and/or actuate independently.

The present disclosure provides fitting assemblies that allow for, but do not require, steep cone angles to be utilized without locking, and additionally allow for, but do not require, matched cone angles to be utilized without locking. This allows the parts of the fitting assemblies to be separated without destroying the parts. Thus, in certain embodiments the first externally tapered portion and the second externally tapered portion of the ferrule have an angle of between about 8° and about 60° or more included angle, between about 8° and about 55° included angle, between about 8° and about 50° included angle, between about 8° and about 45° included angle, between about 8° and about 40° included angle, between about 8° and about 35° included angle, between about 8° and about 30° included angle, between about 8° and about 25° included angle, between about 8° and about 20° included angle, between about 8° and about 15° included angle, between about 8° and about 10° included angle, between about 10° and about 60° included angle, between about 15° and about 60° included angle, between about 20° and about 60° included angle, between about 25° and about 60° included angle, between about 30° and about 60° included angle, between about 35° and about 60° included angle, between about 40° and about 60° included angle, between about 45° and about 60° included angle, between about 50° and about 60° included angle, between about 55° and about 60° included angle, between about 10° and about 55° included angle, between about 15° and about 50° included angle, between about 20° and about 45° included angle, between about 25° and about 40° included angle, or between about 30° and about 35° included angle.

In further embodiments of the fitting assemblies of the present disclosure, the angle of the first externally tapered portion is about equal to or equal to the angle of the second externally tapered portion of the ferrule. In particular embodiments the angle of the first externally tapered portion and the angle of the second externally tapered portion of the ferrule are about 8°, about 9°, about 10°, about 11°, about 12°, about 13°, about 14°, about 15°, about 16°, about 17°, about 18°, about 19°, about 20°, about 22°, about 24°, about 26°, about 28°, about 30°, about 35°, about 40°, about 45°, about 50°, about 55°, or about 60° or more included angle. In additional embodiments of the fitting assemblies of the present disclosure the internally tapered portion of the passageway in the nut has an angle that is the same as the angle of the first externally tapered portion of the ferrule, or that differs from the angle of the first externally tapered portion of the ferrule by about 0°, about 1°, about 2°, about 3°, about 4°, about 5°, about 6°, about 7°, about 8°, about 9°, or about 10° or more included angle.

In certain aspects of the fitting assemblies of the present disclosure the nut and/or the ferrule comprises a polymer. In various embodiments the nut and/or the ferrule comprises polyetheretherketone ("PEEK"), TEFLON®, TEFZEL®, DELRIN®, polyphenylene sulfide (PPS), polypropylene, or any combination thereof. In further embodiments the nut and/or the ferrule comprises polyetheretherketone, TEFLON®, TEFZEL®, DELRIN®, polyphenylene sulfide (PPS), polypropylene, or any combination thereof that has been reinforced with about 5% to about 40% or more of carbon, carbon fibers, glass fibers, steel fibers, or a combination thereof. In certain embodiments the nut, ferrule and/or the tubing comprises annealed PEEK. In particular embodiments the polymer comprises about 10% to about 30% by weight carbon filled polyetheretherketone or about 10% to about 30% by weight glass fiber filled polyetheretherketone. In other embodiments the nut and/or the ferrule comprises a metal, for example stainless steel. In additional embodiments, one of the nut or the ferrule comprises a polymer, such as polyetheretherketone, and the other of the nut or the ferrule comprises a metal, such as stainless steel. In yet other embodiments the fitting assembly consists essentially of biocompatible materials.

It is believed that the presently described fitting assemblies allow for forces to be distributed over a larger area of the tube, which reduces or prevents deformation of the tubing. Therefore, in certain embodiments the fitting assemblies of the present disclosure further comprise at least one tube extending through the passageways of the nut and the ferrule. In particular embodiments the ferrule contacts the tube without substantially deforming the tube.

In further embodiments at least a portion of the passageway through the nut and/or the ferrule is at least partially coated. In particular embodiments at least a portion of the passageway through the nut and/or the ferrule is at least partially coated with a coating comprising a nickel, silica carbide, copper or diamond coating, or a combination thereof.

The present disclosure therefore provides an analytical instrument system comprising at least one fitting assembly having a nut having a first end and a second end, an externally threaded portion proximal the second end of the nut, having a passageway therethrough, wherein the passageway has an internally tapered portion, the nut having an internal lip proximal the second end of the nut, and wherein the nut defines a slot that extends from the second end of the nut through at least a portion of the externally threaded portion of the nut, and a ferrule having a first end, a first externally tapered portion, a central portion, a second externally tapered portion, and a second end, and having a passageway therethrough, wherein the first externally tapered portion of the ferrule is adapted to securely engage with the internally tapered portion of the passageway in the nut, wherein the first externally tapered portion and the central portion define a ferrule lip that securely engages the internal lip of the nut, wherein the ferrule defines at least a first slot that extends from the first end of the ferrule to at least the ferrule lip, or a nut having a first end, a second end, an externally threaded portion proximal to the second end, and having a passageway therethrough, wherein the passageway has an internally tapered portion having a wide end and a narrow end, and a lip proximal the narrow end of the internally tapered portion of the passageway in the nut, and wherein the nut defines a slot that extends from the second end of the nut through at least a portion of the externally threaded portion, and a ferrule having a first end, a first non-tapered portion, a second non-tapered portion, a first externally tapered portion, a third non-tapered portion, a second externally tapered portion, and a second end, and having a passageway therethrough, wherein the first externally tapered portion of the ferrule is adapted to securely engage with the internally tapered portion of the passageway in the nut, wherein the first non-tapered portion and the second non-tapered portion define a ferrule lip that securely engages the lip of the nut, and wherein the ferrule defines at least a first slot that extends from the first end of the ferrule to at least the third non-tapered portion of the ferrule. In particular embodiments the analytical instrument system comprises a liquid chromatography system, such as an ultra high pressure or ultra high performance liquid chromatography system. In other embodiments the analytical instrument system comprises a high performance or high pressure liquid chromatography system, an ultra high performance or ultra high pressure liquid chromatography system, a mass spectrometry system, a microflow chromatography system, a nanoflow chromatography system, a nano-scale chromatography system, a capillary electrophoresis system, a reverse-phase gradient chromatography system, an ion chromatography system, or a combination thereof.

In addition, the present disclosure provides a method of connecting tubing in an analytical instrument system comprising connecting a fitting assembly comprising a tube extending therethrough to a port, fitting or component of the analytical instrument system, wherein the fitting assembly comprises a nut having a first end and a second end, an externally threaded portion proximal the second end of the nut, having a passageway therethrough, wherein the passageway has an internally tapered portion, the nut having an internal lip proximal the second end of the nut, and wherein the nut defines a slot that extends from the second end of the nut through at least a portion of the externally threaded portion of the nut, and a ferrule having a first end, a first externally tapered portion, a central portion, a second externally tapered portion, and a second end, and having a passageway therethrough, wherein the first externally tapered portion of the ferrule is adapted to securely engage with the internally tapered portion of the passageway in the nut, wherein the first externally tapered portion and the central portion define a ferrule lip that securely engages the internal lip of the nut, wherein the ferrule defines at least a first slot that extends from the first end of the ferrule to at least the ferrule lip, or a nut having a first end, a second end, an externally threaded portion proximal to the second end, and having a passageway therethrough, wherein the passageway has an internally tapered portion having a wide end and a narrow end, and a lip proximal the narrow end of the internally tapered portion of the passageway in the nut, and wherein the nut defines a slot that extends from the second end of the nut through at least a portion of the externally threaded portion, and a ferrule having a first end, a first non-tapered portion, a second non-tapered portion, a first externally tapered portion, a third non-tapered portion, a second externally tapered portion, and a second end, and having a passageway therethrough, wherein the first externally tapered portion of the ferrule is adapted to securely engage with the internally tapered portion of the passageway in the nut, wherein the first non-tapered portion and the second non-tapered portion define a ferrule lip that securely engages the lip of the nut, and wherein the ferrule defines at least a first slot that extends from the first end of the ferrule to at least the third non-tapered portion of the ferrule, wherein the fitting or component comprises a first end, an internally threaded portion, and an internally tapered portion, a second end and a passageway therethrough, and wherein the internally threaded portion of the fitting or component is adapted to securely engage with the externally threaded portion of the nut, and wherein the internally tapered portion of the fitting or component is adapted to receive and hold the second externally tapered portion of the ferrule. In certain embodiments the ferrule contacts the tube without substantially deforming the tube.

These and other embodiments and advantages of the disclosed fitting assemblies are described below.

DETAILED DESCRIPTION

Figure 1:
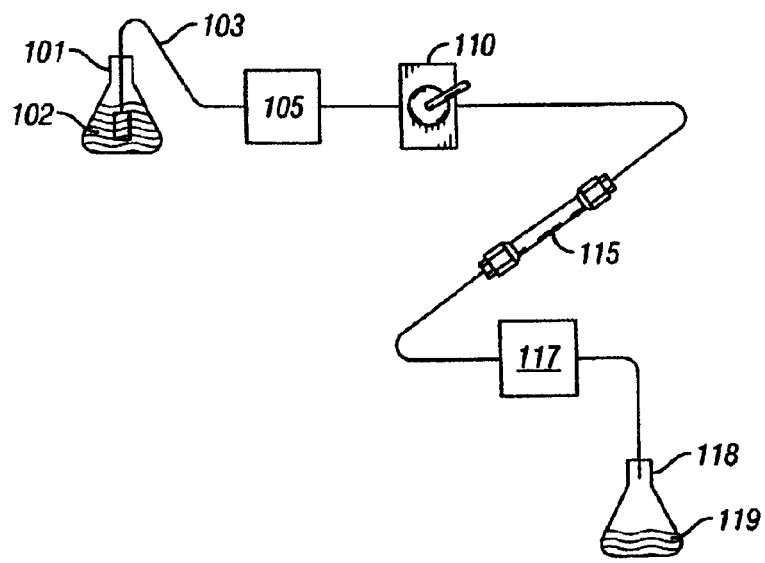
FIG. 1 is a block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well-known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of the synthetic polymer polyetheretherketone, which is commercially available under the trademark PEEK™ from VICTREX®. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
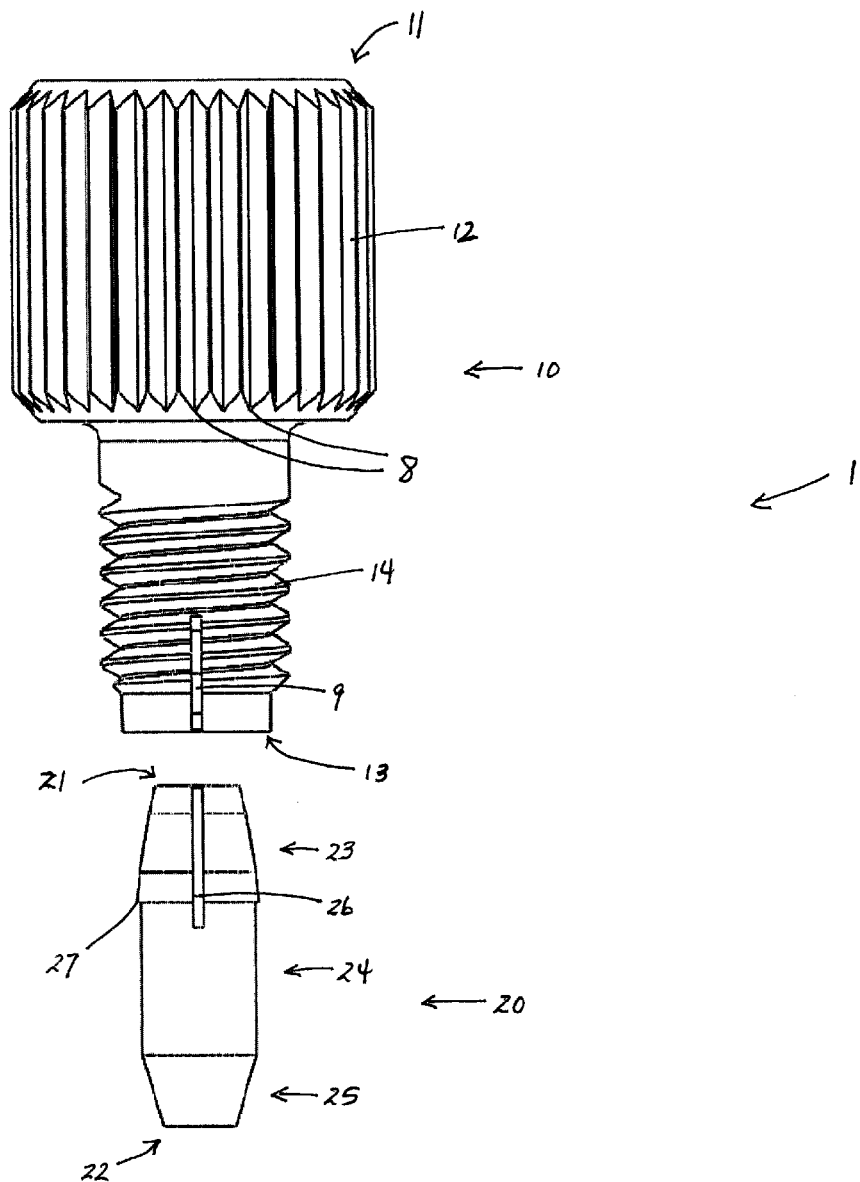
FIG. 2 is an exploded side view of various components of an embodiment of a fitting assembly in accordance with one aspect of the present invention.

Referring now to FIG. 2, a first embodiment of a fitting assembly 1 is shown. As shown in FIG. 2, the assembly 1 includes a nut 10 and a ferrule 20. Nut 10 comprises nut head 12, which is proximal to the first end 11 of the nut 10. An externally threaded portion 14 is proximal to the other or second end 13 of the nut 10. Nut 10 also comprises slot 9, which in this particular embodiment extends from the second end 13 of the nut 10 through a portion of threaded portion 14. Although only one slot is shown in the nut 10 shown in FIG. 2, nut 10 can comprise a plurality of slots, which can extend any distance through the nut 10 from the second end 13 up to but not including the nut head 12 of the nut 10. As shown in FIG. 2, nut 10 and ferrule 20 are preferably circular and symmetric about a center axis. Those skilled in the art will realize that a circular shape has advantages, but the outer diameters in particular of nut head 12 may have a non-circular shape if desired, such as having flat or concave surface portions, to allow an operator to more easily grip and rotate nut 10. In addition, although a plurality of splines 8 are shown on nut head 12 in FIG. 2, the number and presence of such splines are optional, as is the circular design of nut head 12. As detailed herein, the externally threaded portion 14 of the nut 10 is adapted to be removably secured to a corresponding threaded portion of a port, a fitting, or a component of an LC or other analytical instrument (AI) system (not shown). Those skilled in the art will appreciate that the externally threaded portion 14 of the nut 10 may be adapted so that it can be removably engaged with any sized port, fitting, or component of an LC or other AI system (not shown). The use of external threads on one element, such as the nut 10, versus internal threads, is a matter of selection. Those skilled in the art will therefore appreciate that the nut 10 in an alternative embodiment could have internal threads (not shown) located near a second end which could be engaged with external threads (not shown) located near the first end of an alternative embodiment of a port, fitting, or component of an LC or AI system (not shown).

Still referring to FIG. 2, it can be seen that the ferrule 20 as shown has a first end 21 and a second end 22, and three relatively distinct portions. These include a first tapered portion 23, a middle non-tapered portion 24, and a second tapered portion 25. The first tapered portion 23 and second tapered portion 25 each form a truncated conical shape. As shown in FIG. 2, the first tapered portion 23 and the second tapered portion 25 each define an angle from the axis of the ferrule 20. However, those skilled in the art will appreciate that the first tapered portion 23 and second tapered portion 25 can define a different angle if desired, and can define angles that are about equal to each other, or differ from each other, depending upon the particular application. As detailed herein, the first tapered portion 23 of the ferrule 20 is adapted to be removably received in an internally tapered portion (not shown) of a passageway (not shown) through nut 10, and the second tapered end 25 of the ferrule 20 is adapted to be removably received in a port, fitting, or component of a LC or AI system (not shown). Also shown is this embodiment of ferrule 20 is a slot 26 extending from the first end 21 through the first tapered portion 23 and into the middle non-tapered portion 24 of the ferrule 20, although in alternate embodiments the slot 26 can extend to a greater or lesser extent from the first end 21 of ferrule 20. Although only one slot 26 is shown in the ferrule 20 shown in FIG. 2, ferrule 20 can comprise a plurality of slots, each of which can extend any distance through the ferrule 20 from the first end 21 up to but not including the second end 22 of the ferrule 20. Additionally, ferrule lip 27 is shown at the interface of the first tapered portion 23 and middle non-tapered portion 24.

In general, it is believed that the externally threaded portion 14 of the nut 10 and the shape and size of the second tapered portion 25 of the ferrule 20 should be of a shape and size so that assembled fitting assembly 1 may be easily secured to a port, fitting, or component of a LC or AI system (not shown) and may also be easily removed therefrom, in either case by rotating the nut head 12 (and thereby fitting assembly 1) relative to the port, fitting, or component.

Generally, the rotational force or torque applied to connect to the nut 10, ferrule 20, and tubing extending therethrough (not shown) to a port, fitting, or component in an LC or AI system accomplishes two major tasks. First, the force of the connection of the fitting assembly 1 needs to be sufficient to provide a sealed and leak proof connection to the port, fitting, or component. In addition, the force of the connection of the fitting assembly 1 needs to be sufficient so that the tubing is securely held and is sufficient to prevent detachment due to the hydraulic force of the fluid moving through the tubing. We believe that the latter function typically involves greater forces than the former. We believe that the fitting assembly 1 (such as shown in FIG. 2) provides an advantage in that it allows for better connections at higher pressures without requiring higher forces to connect fitting assembly 1, and without substantial deformation of the tubing.

Figure 3:
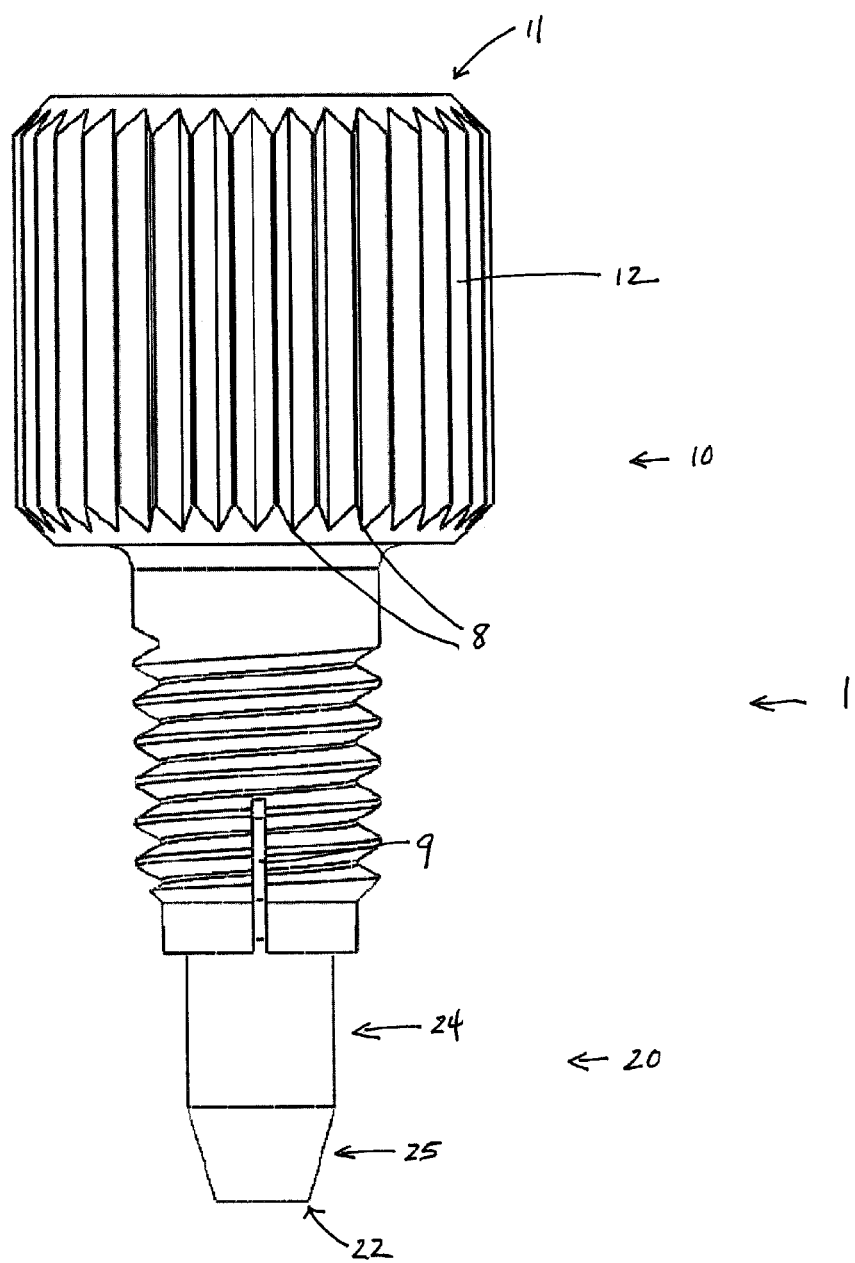
FIG. 3 is a side view of the fitting assembly of FIG. 2 when assembled.

FIG. 3 shows the fitting assembly 1 shown in FIG. 2 upon assembly. Like features and elements in the drawings have the same numerals in the various figures. Upon assembly of fitting assembly 1 only the nut 10, a portion of the middle non-tapered portion 24, and the second tapered portion 25 of ferrule 20 are visible. Additionally, first tapered portion 23 and ferrule lip 27 of the ferrule 20 are not visible, as these elements are positioned within a passageway (not shown) within the nut 10. Still visible upon assembly of the fitting assembly 1 are first end 11, second end 13, nut head 12, splines 8, externally threaded portion 14, and slot 9 of the nut 10, and a portion of the middle non-tapered portion 24, the second tapered portion 25, and the second end 22 of the ferrule 20.

Figure 4:
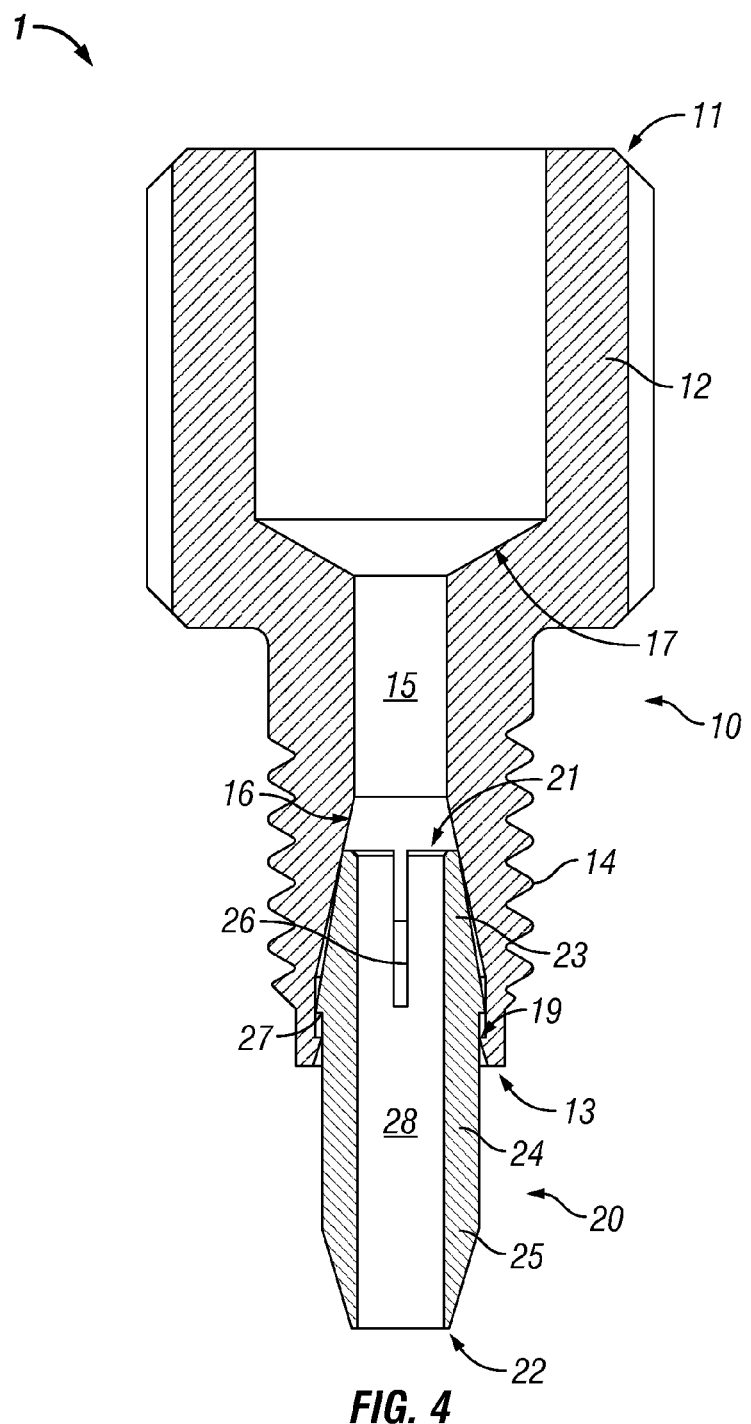
FIG. 4 is a cross-sectional view of the fitting assembly of FIG. 3.

Additional details of the fitting assembly 1 shown in FIG. 3 are shown in the cross-section of the fitting assembly 1 in FIG. 4. Nut 10 has a first end 11, a nut head 12, a second end 13, and an externally threaded portion 14. Passageway 15 extends through nut 10 and includes an internally tapered portion 16. The internally tapered portion 16 of the passageway 15 of the nut 10 is adapted to receive and securely hold the first tapered portion 23 of the ferrule 20 when the fitting assembly 1 is assembled. As shown in FIG. 4, a lip 19 is comprised within passageway 15 near the second end 13 of the nut 10. The externally threaded portion 14 of the nut 10 is adapted to be removably secured to a corresponding threaded portion of a port, a fitting, or a component of an LC or other analytical instrument (AI) system (not shown). Also shown in FIG. 4 is an optional internally tapered portion 17 in passageway 15 near the portion of the nut head 12 distal to the first end 11 of the nut 10. Ferrule 20 has a first end 21, a second end 22, a first tapered portion 23, a middle non-tapered portion 24, a second tapered portion 25, a slot 26, a ferrule lip 27, and a passageway 28, which extends through the ferrule 20. As detailed herein, the internally tapered portion 16 of the passageway 15 and lip 19 of the nut 10 are adapted to receive and securely hold the first tapered portion 23 and ferrule lip 27 of the ferrule 20.

It will be appreciated that the nut 10 and ferrule 20 can comprise a number of different materials. For example, nut 10 and/or ferrule 20 in fitting assembly 1 can comprise a metal, such as stainless steel, or each can comprise a different material, such as a polymer. For example, the fitting assembly 1 can comprise a nut 10 comprising a polymer, such as polyetheretherketone (PEEK), and a ferrule 20 comprising stainless steel. It will be appreciated that a variety of metals and polymers may be selected for either nut 10 or ferrule 20 depending on the particular application, as that may involve a particular type of sample, a particular type of solvent, and/or a particular pressure range. In addition, the selection of materials for the tubing, such as PEEK, PEEKsil™, stainless steel, or fused silica, may lead to a selection of a particular material for nut 10 and/or ferrule 20. In addition, PEEK (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that fitting assembly 1 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In certain applications utilizing PEEK, the PEEK used in fabrication of the nut 10, ferrule 20, and/or tubing may be annealed according to manufacturer's recommendations. In general, the PEEK is ramped from about 70° F. to between about 300° F. and about 320° F. over about 40 to about 60 minutes, held at about 300° F. to about 320° F. for about 150 to about 180 minutes, ramped from between about 300° F. and about 320° F. to between about 392° F. and about 560° F. over about 90 minutes to about 300 minutes, held between about 392° F. and about 560° F. for between about 240 minutes and about 2880 minutes, and ramped down to between about 70° F. and about 284° F. over about 360 minutes to about 600 minutes. However, the skilled artisan will readily understand that different annealing protocols may be used in other applications.

In order for a fitting assembly to seal, it should generally remain in compression (relative to the conical surface of the port) throughout all environmental conditions. Therefore, in certain aspects a coating with a high coefficient of friction is applied to at least a portion of the internal bore surface of the described fitting assembly 1. The high coefficient of friction between the outer surface of the tube and the internal bore surface of the fitting connection or assembly 1 keeps the tube from extruding out of the port during pressurization, which results in dramatically increased burst pressure. In such embodiments the fitting connection or assembly is coated at the internal bore surface that contacts the tube starting at approximately 0.005 inches, about 0.0075 inches, about 0.01 inches, or about 0.02 inches from the tip. Coatings suitable for use with the presently described fitting connection or assembly include, but are not limited to, nickel, silica carbide, copper, and diamond coatings, and combinations thereof.

Methods of using the fitting assembly 1 (such as shown in FIG. 2 and FIG. 3) are now described in further detail. An operator can first provide a nut 10 and ferrule, as well as tubing (not shown). In one approach, the operator can insert a portion of the tubing through the passageways 15 and 28 of the nut 10 and ferrule 20, respectively, in any order without assembling or otherwise connecting the nut 10 and ferrule 20. Next, the operator can insert the first tapered portion 23 of the ferrule 20 into the passageway 15 proximal the second end 13 of the nut 10, such that the first tapered portion 23 of the ferrule 20 pushes against the internal tapered portion 16 of the passageway 15 of the nut 10, and the ferrule lip 27 of the ferrule 20 is retained within the passageway 15 of the nut 10 by lip 19. The operator can then engage the externally threaded portion 14 of the nut 10 with the internally threaded portion of a port, fitting, or component of a LC or AI system (not shown). Once the externally threaded portion 14 of the nut 10 and the internally threaded portion of the port, fitting, or component of a LC or AI system begin to mate or engage, the operator then rotates the nut head 12 of the fitting assembly 1 relative to the port, fitting, or component of a LC or AI system, rotates the port, fitting, or component of a LC or AI system relative to the nut head 12 of the fitting assembly 1, or rotates both the nut head 12 of the fitting assembly 1 and the port, fitting, or component of a LC or AI system relative to each other. By so rotating the nut head 12 of the fitting assembly 1 and the port, fitting, or component of a LC or AI system relative to one another, the operator drives the ferrule 20 further into the interior passageway 15 of the nut 10. In doing so, the operator thus forces the first tapered portion 23 of the ferrule 20 against the internally tapered portion 16 of the passageway 15 of nut 10, thus engaging the ferrule lip 27 of the ferrule 20 with the lip 19 of the passageway 15 of the nut 10. In doing so, the first tapered portion 23 of the ferrule 20 is compressed and held firmly against the internally tapered portion 16 of the passageway 15 of the nut 10, thereby forming a leak proof connection. Because the first tapered portion 23 of the ferrule 20 may be deformed or compressed as it is forced against the tapered portion 16 of the passageway 15 of the nut 10, a leak proof connection may be obtained by the operator without the use of additional tools such as a wrench, pliers or the like, although tools, such as a torque wrench, may be used in certain applications. Alternatively, fitting assembly 1 can be provided to the operator pre-assembled. In one specific embodiment, when tubing having an outer diameter of 0.0625 inches is used, the minimum diameter of the passageway in the fitting assembly can range between about 0.065 and about 0.067 inches.

To disconnect a fitting assembly 1, such as shown in FIG. 2 and FIG. 3, an operator may either rotate the fitting assembly 1 relative to the port, fitting, or component of a LC or AI system (not shown), rotate the port, fitting, or component of a LC or AI system relative to the fitting assembly 1, or rotate both the port, fitting, or component of a LC or AI system and the fitting assembly 1 relative to each other. By rotating the port, fitting, or component of a LC or AI system and/or the fitting assembly 1 relative to one another, the operator thus rotates the externally threaded portion 14 of nut 10 and the internally threaded portion of the port, fitting, or component of a LC or AI system, respectively, and thereby disengages the connection between such threaded portions. At this point, the operator can use the assembly 1 and the leak proof connection it provides, until the operator decides to remove the tubing (not shown) from the assembly 1. By selecting the direction of the threading of the externally threaded portion 14 of the nut 10 and internally threaded portion of the port, fitting, or component of a LC or AI system, respectively, the operator can turn the entire fitting assembly 1 (when connected) by turning or rotating nut 10, such that the fitting assembly 1 rotates relative to the port, fitting, or component of a LC or AI system (not shown) and disengages therefrom. Thus, the entire fitting assembly 1 is easily disconnected from the port, fitting, or component of a LC or AI system (not shown).

Figure 5:
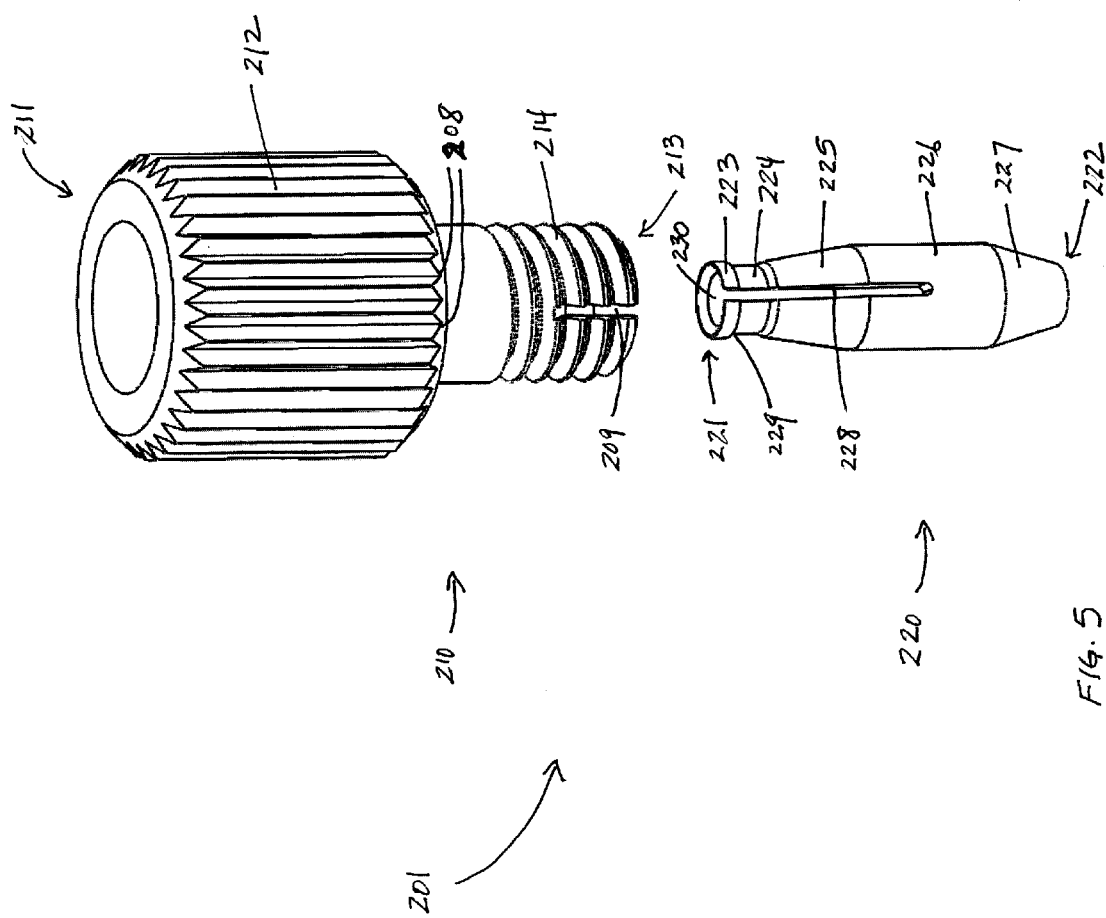
FIG. 5 is an exploded view of various components of an alternate embodiment of a fitting assembly in accordance with one aspect of the present invention.

Referring now to FIG. 5, an alternate embodiment of a fitting assembly 201 is shown. As shown in FIG. 5, the assembly 201 includes a nut 210 and a ferrule 220. Nut 210 comprises nut head 212, which is proximal to the first end 211 of the nut 210. An externally threaded portion 214 is proximal to the other or second end 213 of the nut 210. Nut 210 also comprises slot 209, which in this particular embodiment extends from the second end 213 of the nut 210 through a portion of threaded portion 214. Although only one slot is shown in the nut 210 shown in FIG. 5, nut 210 can comprise a plurality of slots, which can extend any distance through the nut 210 from the second end 213 up to but not including the nut head 212 of the nut 210. As shown in FIG. 5, nut 210 and ferrule 220 are preferably circular and symmetric about a center axis. Those skilled in the art will realize that a circular shape has advantages, but the outer diameters in particular of nut head 212 may have a non-circular shape if desired, such as having flat or concave surface portions, to allow an operator to more easily grip and rotate nut 210. In addition, although a plurality of splines 208 are shown on nut head 212 in FIG. 5, the number and presence of such splines are optional, as is the circular design of nut head 212. As detailed herein, the externally threaded portion 214 of the nut 210 is adapted to be removably secured to a corresponding threaded portion of a port, a fitting, or a component of an LC or other analytical instrument (AI) system (not shown). Those skilled in the art will appreciate that the externally threaded portion 214 of the nut 210 may be adapted so that it can be removably engaged with any sized port, fitting, or component of an LC or other AI system (not shown). The use of external threads on one element, such as the nut 210, versus internal threads, is a matter of selection. Those skilled in the art will therefore appreciate that the nut 210 in an alternative embodiment could have internal threads (not shown) located near a second end which could be engaged with external threads (not shown) located near the first end of an alternative embodiment of a port, fitting, or component of an LC or AI system (not shown).

Still referring to FIG. 5, it can be seen that the ferrule 220 as shown has a first end 221 and a second end 222, and five relatively distinct portions. These include a first non-tapered portion 223, a second non-tapered portion 224, a first tapered portion 225, a third non-tapered portion 226, and a second tapered portion 227. The first tapered portion 225 and second tapered portion 227 each form a truncated conical shape. As shown in FIG. 5, the first tapered portion 225 and the second tapered portion 227 each define an angle from the axis of the ferrule 220. However, those skilled in the art will appreciate that the first tapered portion 225 and second tapered portion 227 can define a different angle if desired, and can define angles that are about equal to each other, or differ from each other, depending upon the particular application. As detailed herein, the first tapered portion 225 of the ferrule 220 is adapted to be removably received in an internally tapered portion (not shown) of a passageway (not shown) through nut 210, and the second tapered portion 227 of the ferrule 220 is adapted to be removably received in a port, fitting, or component of a LC or AI system (not shown). Also shown is this embodiment of ferrule 220 is a slot 228 extending from the first end 221 through the first non-tapered portion 223, second non-tapered portion 224, first tapered portion 225, and into the third non-tapered portion 226 of the ferrule 220, although in alternate embodiments the slot 228 can extend to a greater or lesser extent from the first end 221 of ferrule 220. Although only one slot 228 is shown in the ferrule 220 shown in FIG. 5, ferrule 220 can comprise a plurality of slots, each of which can extend any distance through the ferrule 220 from the first end 221 up to but not including the second end 222 of the ferrule 220. Additionally shown in FIG. 5 are ferrule lip 229, which is defined by the interface of the first non-tapered portion 223 and the second non-tapered portion 224, and passageway 230 through ferrule 220.

In general, it is believed that the externally threaded portion 214 of the nut 210 and the shape and size of the second tapered portion 227 of the ferrule 220 should be of a shape and size so that assembled fitting assembly 201 may be easily secured to a port, fitting, or component of a LC or AI system (not shown) and may also be easily removed therefrom, in either case by rotating the nut head 212 (and thereby fitting assembly 201) relative to the port, fitting, or component.

Generally, the rotational force or torque applied to connect to the nut 210, ferrule 220, and tubing extending therethrough (not shown) to a port, fitting, or component in an LC or AI system accomplishes two major tasks. First, the force of the connection of the fitting assembly 201 needs to be sufficient to provide a sealed and leak proof connection to the port, fitting, or component. In addition, the force of the connection of the fitting assembly 201 needs to be sufficient so that the tubing is securely held and is sufficient to prevent detachment due to the hydraulic force of the fluid moving through the tubing. It is believed that the latter function typically involves greater forces than the former. It is also believed that the fitting assembly 201 (such as shown in FIG. 5) provides an advantage in that it allows for better connections at higher pressures without requiring higher forces to connect fitting assembly 201, and without substantial deformation of the tubing.

Figure 6:
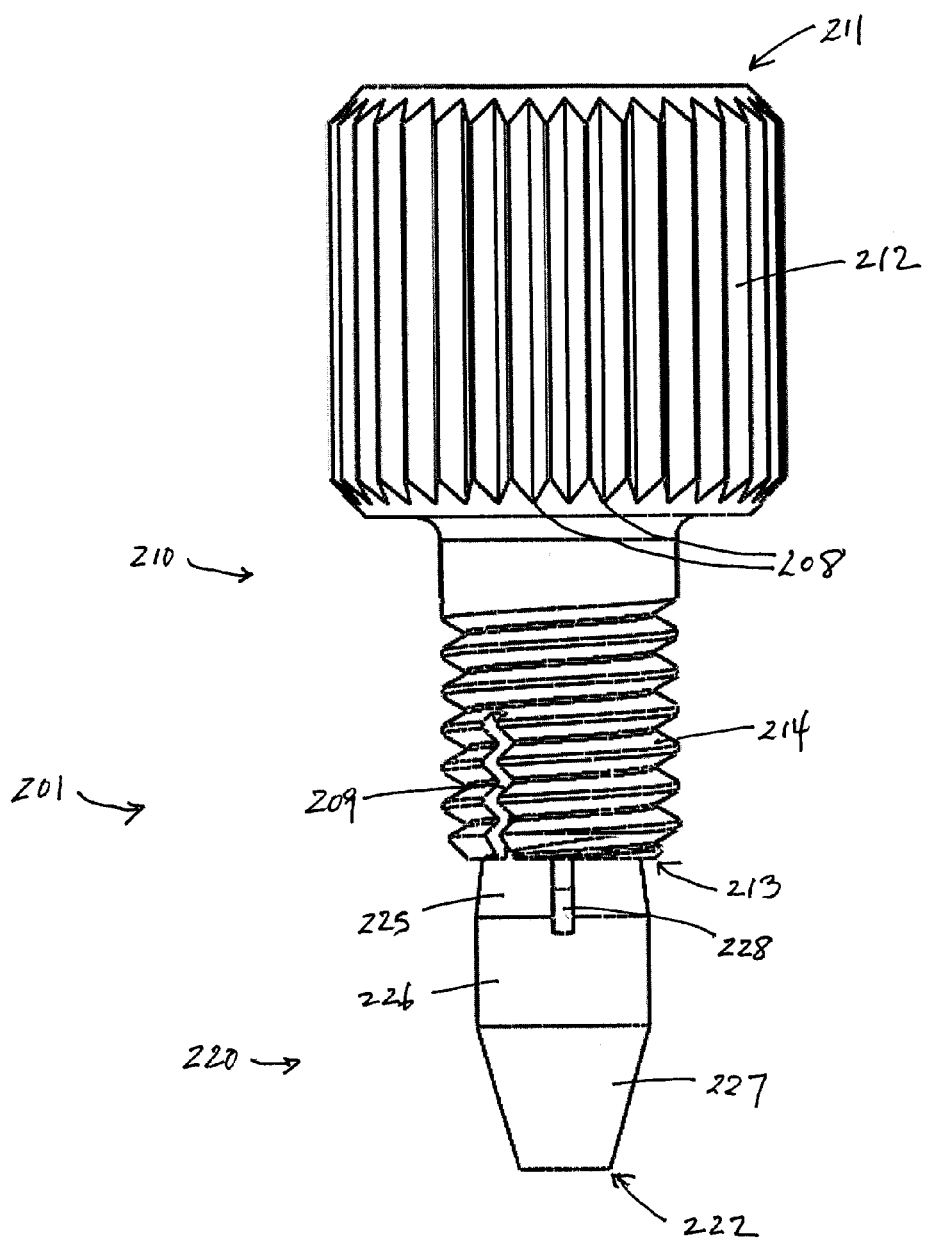
FIG. 6 is a side view of the fitting assembly of FIG. 5 when assembled.

FIG. 6 shows the fitting assembly 201 shown in FIG. 5 upon assembly. Like features and elements in the drawings have the same numerals in the various figures. Upon assembly of fitting assembly 201 only nut 210 and a portion of the first tapered portion 225, a portion of the slot 228, the third non-tapered portion 226 and the second tapered portion 227 of ferrule 220 are visible. Additionally, the first non-tapered portion 223, second non-tapered portion 224, first tapered portion 225 and ferrule lip 229 of the ferrule 220 are not visible, as these elements are positioned within the passageway (not shown) of the nut 210. Still visible upon assembly of the fitting assembly 201 are first end 211, second end 213, nut head 212, splines 208, externally threaded portion 214, and slot 209 of the nut 210, and a portion of the first tapered portion 225, a portion of the slot 228, the third non-tapered portion 226, the second tapered portion 227, and the second end 222 of the ferrule 220.

Figure 7:
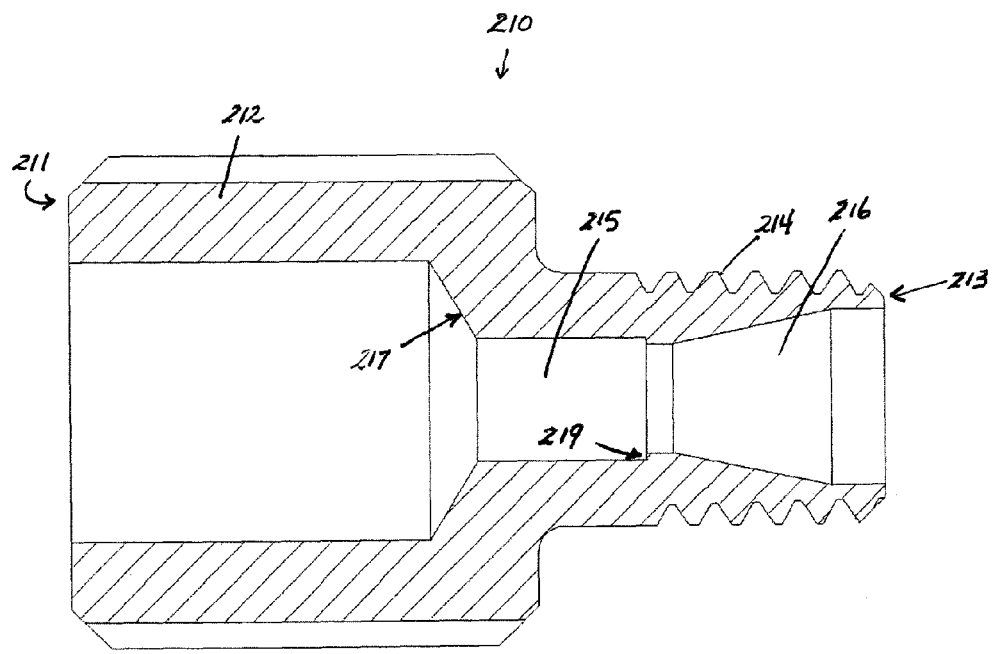
FIG. 7 is cross-sectional view of the nut of FIG. 5.

Additional details of the nut 210 of the fitting assembly 201 shown in FIG. 5 are shown in the cross-section of the nut 210 of the fitting assembly 201 in FIG. 7. Nut 210 has a first end 211, a nut head 212, a second end 213, and an externally threaded portion 214. Passageway 215 extends through nut 210 and includes an internally tapered portion 216. The internally tapered portion 216 of the passageway 215 of the nut 210 is adapted to receive and securely hold the first tapered portion 225 of the ferrule 220 when the fitting assembly 201 is assembled. As shown in FIG. 7, a lip 219 is comprised within passageway 215 near the narrow portion of the internally tapered portion 216 of the passageway 215 of the nut 210. The externally threaded portion 214 of the nut 210 is adapted to be removably secured to a corresponding threaded portion of a port, a fitting, or a component of an LC or other analytical instrument (AI) system (not shown). Also shown in FIG. 7 is an optional internally tapered portion 217 in passageway 215 near the portion of the nut head 212 distal to the first end 211 of the nut 210.

Figure 8:
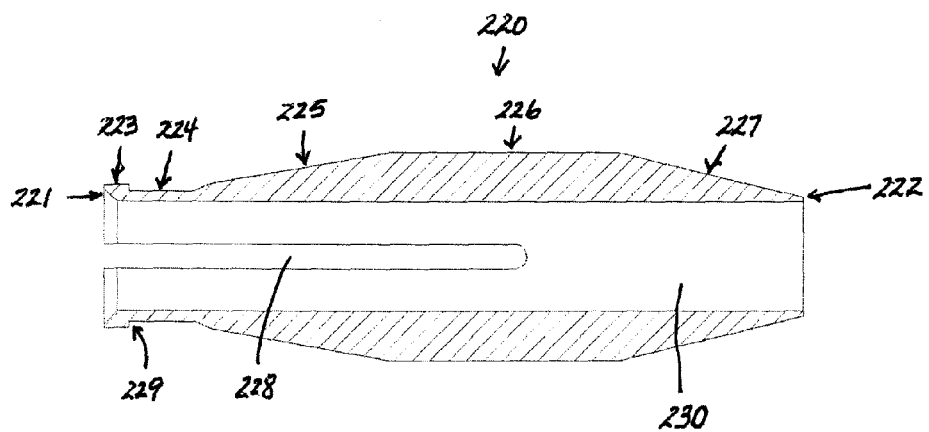
FIG. 8 is cross-sectional view of the ferrule of FIG. 5.

Additional details of the ferrule 220 of the fitting assembly 201 shown in FIG. 5 are shown in the cross-section of the ferrule 220 of the fitting assembly 201 in FIG. 8. Ferrule 220 has a first end 221, a second end 222, a first non-tapered portion 223, a second non-tapered portion 224, a first tapered portion 225, a third non-tapered portion 226, a second tapered portion 227, a slot 228, a ferrule lip 229, and a passageway 230, which extends through the ferrule 220. As detailed herein, the internally tapered portion 216 of the passageway 215 and lip 219 of the nut 210 are adapted to receive and securely hold the first tapered portion 225 and ferrule lip 229 of the ferrule 220.

Figure 9:
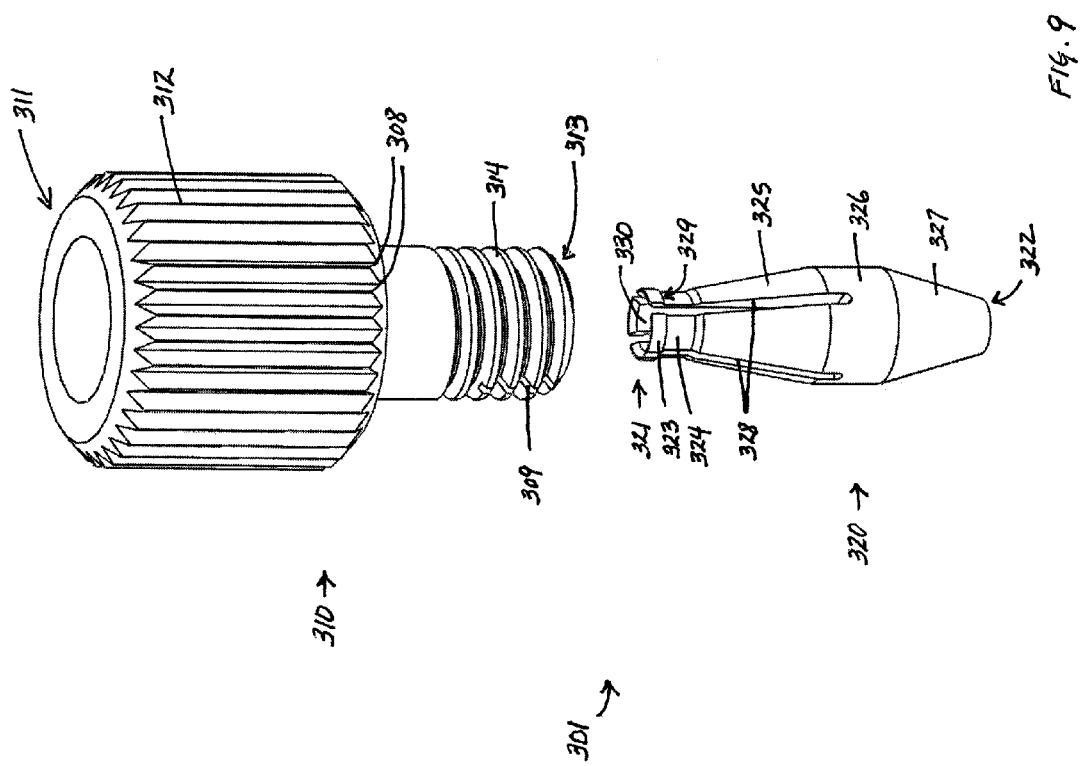
FIG. 9 is an exploded view of various components of an alternate embodiment of a fitting assembly in accordance with one aspect of the present invention.

Referring now to FIG. 9, an alternate embodiment of a fitting assembly 301 is shown. As shown in FIG. 9, the assembly 301 includes a nut 310 and a ferrule 320. Nut 310 comprises nut head 312, which is proximal to the first end 311 of the nut 310. An externally threaded portion 314 is proximal to the other or second end 313 of the nut 310. Nut 310 also comprises slot 309, which in this particular embodiment extends from the second end 313 of the nut 310 through a portion of threaded portion 314. Although only one slot is shown in the nut 310 shown in FIG. 9, nut 310 can comprise a plurality of slots, which can extend any distance through the nut 310 from the second end 313 up to but not including the nut head 312 of the nut 310. As shown in FIG. 9, nut 310 and ferrule 320 are preferably circular and symmetric about a center axis. Those skilled in the art will realize that a circular shape has advantages, but the outer diameters in particular of nut head 312 may have a non-circular shape if desired, such as having flat or concave surface portions, to allow an operator to more easily grip and rotate nut 310. In addition, although a plurality of splines 308 are shown on nut head 312 in FIG. 9, the number and presence of such splines are optional, as is the circular design of nut head 312. As detailed herein, the externally threaded portion 314 of the nut 310 is adapted to be removably secured to a corresponding threaded portion of a port, a fitting, or a component of an LC or other analytical instrument (AI) system (not shown). Those skilled in the art will appreciate that the externally threaded portion 314 of the nut 310 may be adapted so that it can be removably engaged with any sized port, fitting, or component of an LC or other AI system (not shown). The use of external threads on one element, such as the nut 310, versus internal threads, is a matter of selection. Those skilled in the art will therefore appreciate that the nut 310 in an alternative embodiment could have internal threads (not shown) located near a second end which could be engaged with external threads (not shown) located near the first end of an alternative embodiment of a port, fitting, or component of an LC or AI system (not shown).

Still referring to FIG. 9, it can be seen that the ferrule 320 as shown has a first end 321 and a second end 322, and five relatively distinct portions. These include a first non-tapered portion 323, a second non-tapered portion 324, a first tapered portion 325, a third non-tapered portion 326, and a second tapered portion 327. The first tapered portion 325 and second tapered portion 327 each form a truncated conical shape. As shown in FIG. 9, the first tapered portion 325 and the second tapered portion 327 each define an angle from the axis of the ferrule 320. However, those skilled in the art will appreciate that the first tapered portion 325 and second tapered portion 327 can define a different angle if desired, and can define angles that are about equal to each other, or differ from each other, depending upon the particular application. As detailed herein, the first tapered portion 325 of the ferrule 320 is adapted to be removably received in an internally tapered portion (not shown) of a passageway (not shown) through nut 310, and the second tapered portion 327 of the ferrule 320 is adapted to be removably received in a port, fitting, or component of a LC or AI system (not shown). Also shown in this embodiment of ferrule 320 is a plurality of slots 328 extending from the first end 321 through the first non-tapered portion 323, second non-tapered portion 324, first tapered portion 325, and into the third non-tapered portion 326 of the ferrule 320, although in alternate embodiments the slot 328 can extend to a greater or lesser extent from the first end 321 of ferrule 320. Although a plurality of slots 328 is shown in the ferrule 320 shown in FIG. 9, ferrule 220 can comprise one slot, which can extend any distance through the ferrule 320 from the first end 321 up to but not including the second end 322 of the ferrule 320. Additionally shown in FIG. 9 are ferrule lip 329, which is defined by the interface of the first non-tapered portion 323 and the second non-tapered portion 324, and passageway 330 through ferrule 320.

In general, it is believed that the externally threaded portion 314 of the nut 310 and the shape and size of the second tapered portion 327 of the ferrule 320 should be of a shape and size so that assembled fitting assembly 301 may be easily secured to a port, fitting, or component of a LC or AI system (not shown) and may also be easily removed therefrom, in either case by rotating the nut head 312 (and thereby fitting assembly 301) relative to the port, fitting, or component.

Generally, the rotational force or torque applied to connect to the nut 310, ferrule 320, and tubing extending therethrough (not shown) to a port, fitting, or component in an LC or AI system accomplishes two major tasks. First, the force of the connection of the fitting assembly 301 needs to be sufficient to provide a sealed and leak proof connection to the port, fitting, or component. In addition, the force of the connection of the fitting assembly 301 needs to be sufficient so that the tubing is securely held and is sufficient to prevent detachment due to the hydraulic force of the fluid moving through the tubing. It is believed that the latter function typically involves greater forces than the former. It is also believed that the fitting assembly 301 (such as shown in FIG. 9) provides an advantage in that it allows for better connections at higher pressures without requiring higher forces to connect fitting assembly 301, and without substantial deformation of the tubing.

Figure 10:
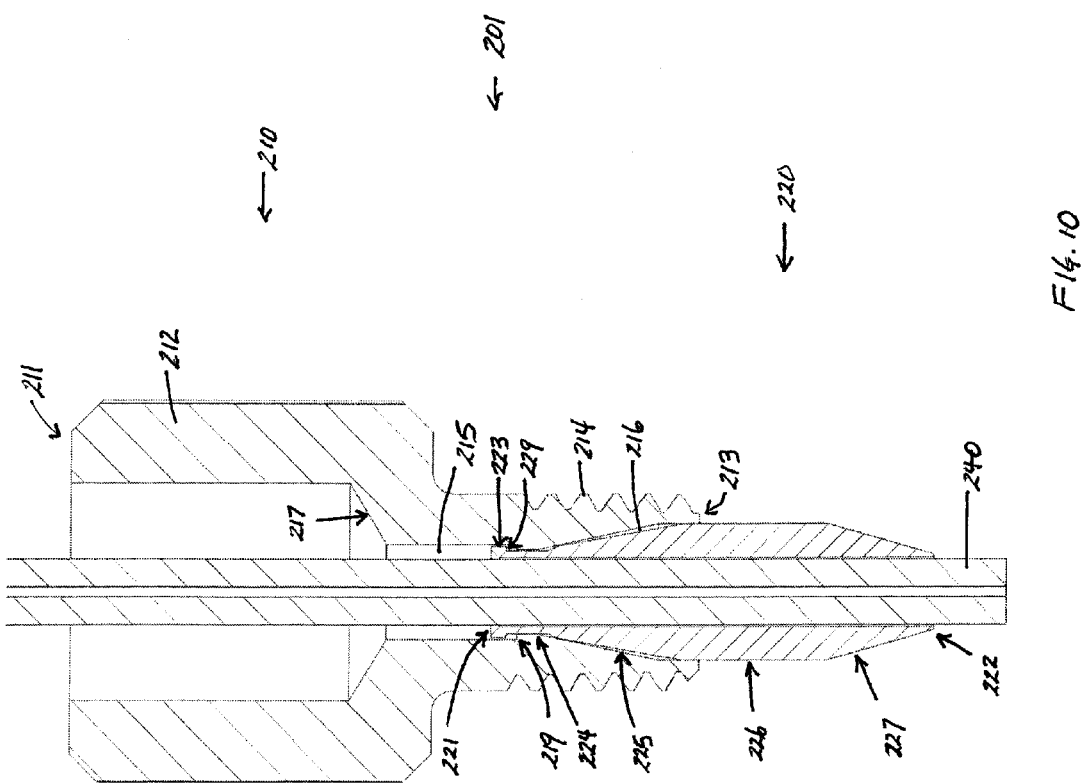
FIG. 10 is a cross-sectional view of the fitting assembly of FIG. 5 when assembled, with a tube extending through the nut and ferrule.

FIG. 10 shows a cross-section of the fitting assembly 201 shown in FIG. 5 upon assembly, with a tube 240 extending through the nut 210 and ferrule 220. Nut 210 has a first end 211, a nut head 212, a second end 213, and an externally threaded portion 214. Passageway 215 extends through nut 210 and includes an internally tapered portion 216. The internally tapered portion 216 of the passageway 215 of the nut 210 is adapted to receive and securely hold the first tapered portion 225 of the ferrule 220 when the fitting assembly 201 is assembled. As shown in FIG. 10, a lip 219 is comprised within passageway 215 near the narrow portion of the internally tapered portion 216 of the passageway 215 of the nut 210. The externally threaded portion 214 of the nut 210 is adapted to be removably secured to a corresponding threaded portion of a port, a fitting, or a component of an LC or other analytical instrument (AI) system (not shown). Also shown in FIG. 10 is an optional internally tapered portion 217 in passageway 215 near the portion of the nut head 212 distal to the first end 211 of the nut 210. Ferrule 220 has a first end 221, a second end 222, a first non-tapered portion 223, a second non-tapered portion 224, a first tapered portion 225, a third non-tapered portion 226, a second tapered portion 227, a slot (not visible), a ferrule lip 229, and a passageway (not visible), which extends through the ferrule 220. As detailed herein, the internally tapered portion 216 of the passageway 215 and lip 219 of the nut 210 are adapted to receive and securely hold the first tapered portion 225 and ferrule lip 229 of the ferrule 220. Tube 240 is shown extending through passageway 215 of nut 210 and passageway of ferrule 220.

The following example is included to demonstrate preferred embodiments of the invention. It should be appreciated by those of skill in the art that the techniques disclosed in the example which follows represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

Performance of a fitting assembly 1 as described herein, for example as shown in FIG. 2, was tested as detailed below. In the tested fitting assembly 1, the ferrule 20 is captivated in nut 10, yet free to rotate and actuate independently. The slot 26 (or plurality of slots, as detailed below) is designed and adapted to allow the portion of the ferrule 20 proximal to the slot 26 to apply a high enough normal force over a large enough surface area to keep the tube from moving while the fitting assembly 1 is used in service (e.g., when pressure is applied to fluid in the tube once connected in a LC or other AI system), and to keep the tube from being point loaded or permanently deformed by the fingers. In other words, this portion of ferrule 20 applies a radial force on the tube without point loading (as is the case with previous fitting assembly designs), which would leave a sharp mark (an annular groove) that is sometimes visible to the naked eye, and that essentially locks the ferrule 20 and tube together placing them into a shear condition (e.g., in the same situation as if there were a threaded connection). While conventional fitting assemblies may hold the tube quite well, this condition forces the tube to only be used in the port to which it was initially connected (e.g., the port in which deformation occurred), because each port varies slightly due to manufacturing tolerances, and a previously deformed tube with a groove could easily shift out of another port if so connected because the ferrule 20 would likely be essentially guided into the pre-existing groove. This is undesirable because, among other things, such a condition likely adds dead volume to the connection and the LC or AI system. Unlike conventional fittings where such deformation is a problem, in the fitting assembly 1 of this example, there may be deformation (especially when over-tightened on multiple uses), but any such deformation is not found to be in the form of a sharp annular groove in the tube and does not prevent further use of the fitting assembly 1.

In the presently described fitting assembly 1, the region of the ferrule 20 proximal the slot(s) 26 are designed and adapted to deflect radially with minimal force. The material and thickness of the ferrule 20, and the length and quantity of the slots 26 are designed and adapted to allow for the appropriate stiffness to enable the ferrule 20 to function as desired and described. As the internally tapered portion 16 of the nut 10 is forced over the first tapered portion of the ferrule 20 during the formation of a connection, the region of the ferrule 20 proximal the slot(s) 26 easily deflects until the tube is contacted over a relatively large surface area, without permanently deforming the ferrule 20 at the point where the ferrule 20 contacts the tube. Continued force places this portion of the ferrule 20 into compressive loading, which allows the ferrule 20 to securely grip the tube. The spring-like action of this region of the ferrule 20 also allows the ferrule 20 to provide a slight radial force on tubes within a specific outside diameter tolerance (i.e., a ferrule 20 can be placed on a tube with an outer diameter of 0.063 inches or 0.064 inches and lightly grip the tube). This design feature allows the ferrule 20 to remain on a tube without falling off, yet is still easily positioned on the tube by the hand by the operator. Loading over a relatively large area as described also keeps the inner wall of the tube from collapsing in a specific area and creating a flow restriction. Such flow restrictions may lead to turbulent flow and are considered undesirable.

The interface of the first tapered portion 23 of the ferrule 20 to the internally tapered portion 16 of the passageway 15 of the nut 10 is designed and adapted to allow the nut 10 to provide maximum radial force without locking the two tapered portions together. In this example, the first tapered portion 23 of the ferrule 20 is designed to be about 18° included angle and the internally tapered portion 16 of the passageway 15 of the nut 10 is designed to be about 24° included angle (about a 6° mismatch between the tapers (e.g., the tapers are mismatched so that the area at the extreme end of the first tapered portion 23 of the ferrule 20 contacts the internally tapered portion 16 of the nut 10 first). This exemplary design keeps the parts from locking, yet allows the fingers to be loaded and deflected without causing permanent deformation to the ferrule 20, nut 10, or tube that prevents re-use of the fitting assembly 1. In most of the applications of the fitting assembly 1, no marks visible to the naked eye are made on the tube by the ferrule 20. The ferrule tapers are also designed and adapted so that the natural tendency of the tube towards backing out of the port during pressurization of the fluid in the LC or AI system further presses the ferrule 20 against the surface of the tube, thus increasing the normal force and therefore increasing the frictional force restraining the tube. The fitting in this example is also designed and adapted to retain the tubing in the fitting during over-pressurization and vent the pressure without having the tubing extrude entirely from the fitting to prevent harm to the operator.

In testing of assemblies like those shown and described herein, good results have been obtained. In a first test, fitting assemblies similar to those shown in FIG. 2 were assembled, in which the nut 10 was made of annealed PEEK and the ferrule 20 was made of unfilled PEEK. PEEK tubing was used in the test. In the test, a calibrated torque wrench was used to measure the torque applied to the test fitting assemblies. A standard union (P-779; commercially available from IDEX Health and Science, Oak Harbor, Wash.) was used, as this was determined to be representative of actual use of the fitting assembly, and the burst pressure was measured. Results are shown below in Table 1.

TABLE 1

| Sample | Torque (inch-pounds) | Burst Pressure (psi) | Notes |
|---|---|---|---|
| 1 | 4.00 | 12,000 | |
| 2 | 4.00 | 12,000 | |
| 3 | 4.00 | 13,400 | |
| 4 | 4.00 | 11,565 | Tube extruded from fitting |
| 5 | 4.00 | 10,639 | Tube extruded from fitting |
| 6 | 4.00 | 13,452 | Tube extruded from fitting |
| 7 | 4.00 | 12,000 | |
| 8 | 4.00 | 12,000 | |
| 9 | 4.00 | 11,144 | Tube extruded from fitting |
| 10 | 4.00 | 11,704 | Tube extruded from fitting |
| 11 | 4.00 | 12,000 | |
| 12 | 4.00 | 10,235 | Tube extruded from fitting |
| 13 | 4.00 | 12,000 | |
| 14 | 4.00 | 14,609 | Tube extruded from fitting |
| 15 | 4.00 | 13,163 | Tube extruded from fitting |

All 15 of the fitting assemblies held pressure to over 10,000 psi, and could achieve 10 assembly cycles when 4 inch-pounds of torque was used to seal the fitting assemblies. Testing also revealed that the tubing was not deformed due to ferrule loading. While the ferrule did occasionally lock into the nut, the ferrule was easily broken free by applying a light side load to the tip of the ferrule. This can be done with the operator's finger or by lightly pressing the ferrule into a surface.

In a second test, fitting assemblies similar to those shown in FIG. 5 were assembled, with the exception that the ferrule had two slots of equal length 180° opposed from each other. These assemblies were tested as described above, and the results are shown below in Table 2.

TABLE 2

| Sample | Torque (inch-pounds) | Burst Pressure (psi) | Notes |
|---|---|---|---|
| 1 | 3.50 | 11,167 | Tube extruded from fitting |
| 2 | 3.50 | 11,728 | Tube extruded from fitting |
| 3 | 3.50 | 11,540 | Tube extruded from fitting |
| 4 | 3.50 | 11,500 | Tube extruded from fitting |
| 5 | 3.50 | 12,548 | Tube extruded from fitting |

All 5 of the fitting assemblies held pressure to over 10,000 psi at 3.50 inch-pounds of torque, with a mean burst pressure of 11,696.6 and a standard deviation of 517.1 psi. Radial force was applied to all five of the ferrules after testing to break them free. Ferrule retention was found to be good in all cases.

In a third test, fitting assemblies similar to those shown in FIG. 5 were assembled, with the exception that the ferrule had three slots of equal length and one slot of shorter length, with the slots 90° opposed from each other. These assemblies were tested as described above, and the results are shown below in Table 3.

TABLE 3

| Sample | Torque (inch-pounds) | Burst Pressure (psi) | Notes |
|---|---|---|---|
| 1 | 3.50 | 12,000 | |
| 2 | 3.50 | 12,309 | Tube extruded from fitting |
| 3 | 3.50 | 12,000 | |
| 4 | 3.50 | 10,468 | Tube extruded from fitting |
| 5 | 3.50 | 10,272 | Tube extruded from fitting |

All 5 of the fitting assemblies held pressure to over 10,000 psi at 3.50 inch-pounds of torque, with a mean burst pressure of 11,409.8 and a standard deviation of 960.1 psi. Radial force was applied to all five of the ferrules after testing to break them free. Ferrule retention was found to be less in all cases than that seen in the two slot ferrule test detailed above.

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:

1. A fitting assembly for use in a liquid chromatography system, comprising:
   a) a nut having a first end, a second end, an externally threaded portion proximal to said second end, and having a passageway therethrough, wherein said passageway has an internally tapered portion having a wide end and a narrow end, and a lip proximal said narrow end of said internally tapered portion of said passageway in said nut, and wherein said nut defines a slot that extends from said second end of said nut through at least a portion of said externally threaded portion; and
   b) a ferrule having a first end, a first non-tapered portion, a second non-tapered portion, a first externally tapered portion, a third non-tapered portion, a second externally tapered portion, and a second end, and having a passageway therethrough, wherein said first externally tapered portion of said ferrule is adapted to securely engage with said internally tapered portion of said passageway in said nut, wherein said first non-tapered portion and said second non-tapered portion define a ferrule lip that securely engages said lip of said nut, and wherein said ferrule defines at least a first slot that extends from said first end of said ferrule to at least said third non-tapered portion of said ferrule.

2. The fitting assembly according to claim 1, wherein said ferrule defines a plurality of slots that extend from said first end of said ferrule to at least said ferrule lip.

3. The fitting assembly according to claim 1, wherein the angle of said first externally tapered portion is equal to the angle of said second externally tapered portion of said ferrule.

4. The fitting assembly according to claim 3, wherein the angle of said first externally tapered portion and the angle of said second externally tapered portion of said ferrule are about 18° included angle.

5. The fitting assembly according to claim 4, wherein the angle of said first externally tapered portion of said ferrule and the angle of said second externally tapered portion of said ferrule are about 18° included angle, and wherein said internally tapered portion of said passageway in said nut has an angle of about 24° included angle.

6. The fitting assembly according to claim 4, wherein said nut or said ferrule comprises polyetheretherketone.

7. The fitting assembly according to claim 1, wherein said internally tapered portion of said passageway in said nut has an angle that differs from the angle of said first externally tapered portion of said ferrule by about 6° included angle.

8. The fitting assembly according to claim 1, further comprising at least one tube extending through the passageways of said nut and said ferrule.

9. The fitting assembly according to claim 8, wherein said ferrule contacts said tube without substantially deforming the tube.

10. An analytical instrument system comprising at least one fitting assembly having:
   a) a nut having a first end, a second end, an externally threaded portion proximal to said second end, and having a passageway therethrough, wherein said passageway has an internally tapered portion having a wide end and a narrow end, and a lip proximal said narrow end of said internally tapered portion of said passageway in said nut, and wherein said nut defines a slot that extends from said second end of said nut through at least a portion of said externally threaded portion; and
   b) a ferrule having a first end, a first non-tapered portion, a second non-tapered portion, a first externally tapered portion, a third non-tapered portion, a second externally tapered portion, and a second end, and having a passageway therethrough, wherein said first externally tapered portion of said ferrule is adapted to securely engage with said internally tapered portion of said passageway in said nut, wherein said first non-tapered portion and said second non-tapered portion define a ferrule lip that securely engages said lip of said nut, and wherein said ferrule defines at least a first slot that extends from said first end of said ferrule to at least said third non-tapered portion of said ferrule.

11. The system according to claim 10, wherein said analytical instrument system comprises an ultra high pressure or ultra high performance liquid chromatography system.

12. A method of connecting tubing in an analytical instrument system comprising:
   connecting a fitting assembly comprising a tube extending therethrough to a port, fitting or component of said analytical instrument system;
   wherein said fitting assembly comprises:
   a) a nut having a first end, a second end, an externally threaded portion proximal to said second end, and having a passageway therethrough, wherein said passageway has an internally tapered portion having a wide end and a narrow end, and a lip proximal said narrow end of said internally tapered portion of said passageway in said nut, and wherein said nut defines a slot that extends from said second end of said nut through at least a portion of said externally threaded portion; and
   b) a ferrule having a first end, a first non-tapered portion, a second non-tapered portion, a first externally tapered portion, a third non-tapered portion, a second externally tapered portion, and a second end, and having a passageway therethrough, wherein said first externally tapered portion of said ferrule is adapted to securely engage with said internally tapered portion of said passageway in said nut, wherein said first non-tapered portion and said second non-tapered portion define a ferrule lip that securely engages said lip of said nut, and wherein said ferrule defines at least a first slot that extends from said first end of said ferrule to at least said third non-tapered portion of said ferrule;

wherein said port, fitting or component comprises a first end, an internally threaded portion, and an internally tapered portion, a second end and a passageway therethrough, and wherein said internally threaded portion of said port, fitting or component is adapted to securely engage with said externally threaded portion of said nut, and wherein the internally tapered portion of said port, fitting or component is adapted to receive and hold said second externally tapered portion of said ferrule.

13. The method according to claim 12, wherein said analytical instrument system comprises an ultra high pressure or ultra high performance liquid chromatography system.

14. The method according to claim 12, wherein said ferrule contacts said tube without substantially deforming the tube.

* * * * *